US012329682B2

(12) United States Patent
Argento et al.

(10) Patent No.: US 12,329,682 B2
(45) Date of Patent: Jun. 17, 2025

(54) ADJUSTABLE FLOW GLAUCOMA SHUNTS AND METHODS FOR MAKING AND USING SAME

(71) Applicant: Shifamed Holdings, LLC, Campbell, CA (US)

(72) Inventors: Claudio Argento, Felton, CA (US); Colin Mixter, Campbell, CA (US); Andrew Backus, Santa Cruz, CA (US)

(73) Assignee: Shifamed Holdings, LLC, Campbell, CA (US)

(*) Notice: Subject to any disclaimer, the term of this patent is extended or adjusted under 35 U.S.C. 154(b) by 0 days.

(21) Appl. No.: 17/422,613

(22) PCT Filed: Jan. 17, 2020

(86) PCT No.: PCT/US2020/014186
§ 371 (c)(1),
(2) Date: Jul. 13, 2021

(87) PCT Pub. No.: WO2020/150663
PCT Pub. Date: Jul. 23, 2020

(65) Prior Publication Data
US 2022/0087865 A1    Mar. 24, 2022

Related U.S. Application Data

(60) Provisional application No. 62/794,430, filed on Jan. 18, 2019.

(51) Int. Cl.
*A61F 9/007* (2006.01)
*A61F 9/00* (2006.01)
*F16K 99/00* (2006.01)

(52) U.S. Cl.
CPC ........ *A61F 9/00781* (2013.01); *A61F 9/0017* (2013.01); *A61M 2205/3341* (2013.01);
(Continued)

(58) Field of Classification Search
CPC .............. A61F 9/000781; A61F 9/0017; A61F 2250/001; A61F 2250/0097;
(Continued)

(56) References Cited

U.S. PATENT DOCUMENTS 4,401,107 A    8/1983   Harber et al.
4,402,681 A    9/1983   Haas et al.
(Continued)

FOREIGN PATENT DOCUMENTS

AU    2014200171         1/2014
AU    2014201621 B2      3/2016
(Continued)

OTHER PUBLICATIONS

International Search Report and Written Opinion received for PCT Application No. PCT/US22/35324, filed on Jun. 28, 2022, Applicant: Shifamed Holdings, LLC, Date of Mailing: Nov. 22, 2022, 12 pages.
(Continued)

*Primary Examiner* — Nicholas J. Weiss
*Assistant Examiner* — Peter Daniel Smith
(74) *Attorney, Agent, or Firm* — Perkins Coie LLP (57) ABSTRACT

Adjustable flow glaucoma shunts are disclosed herein. In one embodiment, for example, a variable flow shunt for treatment of glaucoma in a human patient includes an elongated outflow tube having (a) a proximal inflow portion configured for placement within an anterior chamber in a region outside of an optical field of view of an eye of the patient, and (b) a distal outflow portion at a different location of the eye. The variable flow shunt further includes a flow control mechanism positioned along the outflow tube between the inflow portion and the outflow portion. The flow control mechanism comprises one or more control elements transformable between an open position that allows fluid to
(Continued)

flow through the outflow tube and resistance positions that partially obstruct or attenuate fluid flow through the outflow tube. During operation, the control element(s) are movable between positions in response to non-invasive energy.

15 Claims, 6 Drawing Sheets

(52) U.S. Cl.
CPC .............. *A61M 2210/0612* (2013.01); *F16K 2099/0088* (2013.01)

(58) Field of Classification Search
CPC ... A61M 2205/3341; A61M 2210/0612; F16K 2099/0088
See application file for complete search history.

(56) References Cited

U.S. PATENT DOCUMENTS

| | | |
|---|---|---|
| 4,595,390 A | 6/1986 | Hakim et al. |
| 5,070,697 A | 12/1991 | Van Zeggeren |
| 5,123,906 A | 6/1992 | Kelman |
| 5,300,020 A | 4/1994 | L'Esperance, Jr. |
| 5,476,445 A | 12/1995 | Baerveldt et al. |
| 5,601,094 A | 2/1997 | Reiss |
| 5,792,118 A | 8/1998 | Kurth et al. |
| 6,077,298 A | 6/2000 | Tu et al. |
| 6,077,299 A | 6/2000 | Adelberg et al. |
| 6,203,513 B1 | 3/2001 | Yaron et al. |
| 6,261,256 B1 | 7/2001 | Ahmed |
| 6,450,984 B1 | 9/2002 | Lynch et al. |
| 6,508,779 B1 | 1/2003 | Suson |
| 6,589,203 B1 | 7/2003 | Mitrev |
| 6,626,858 B2 | 9/2003 | Lynch et al. |
| 6,638,239 B1 | 10/2003 | Bergheim |
| 6,666,841 B2 | 12/2003 | Gharib et al. |
| 6,736,791 B1 | 5/2004 | Tu et al. |
| 6,789,447 B1 | 9/2004 | Zinck |
| 7,025,740 B2 | 4/2006 | Ahmed |
| 7,207,965 B2 | 4/2007 | Simon |
| 7,354,416 B2 | 4/2008 | Quiroz-Mereado et al. |
| 7,364,564 B2 | 4/2008 | Sniegowski et al. |
| 7,458,953 B2 | 12/2008 | Peyman |
| 7,699,882 B2 | 4/2010 | Stamper et al. |
| 7,717,872 B2 | 5/2010 | Shetty |
| 7,947,008 B2 | 5/2011 | Grahn et al. |
| 8,012,134 B2 | 9/2011 | Claude et al. |
| 8,206,333 B2 * | 6/2012 | Schmidt .............. A61F 9/00781 604/9 |
| 8,206,440 B2 | 6/2012 | Guarnieri |
| 8,298,240 B2 | 10/2012 | Giger et al. |
| 8,308,701 B2 | 11/2012 | Horvath et al. |
| 8,414,635 B2 | 4/2013 | Hyodoh et al. |
| 8,506,515 B2 | 8/2013 | Burns et al. |
| 8,540,659 B2 | 9/2013 | Berlin |
| 8,579,848 B2 | 11/2013 | Field et al. |
| 8,585,629 B2 | 11/2013 | Grabner et al. |
| 8,663,303 B2 | 3/2014 | Horvath et al. |
| 8,702,639 B2 * | 4/2014 | Van Der Mooren ........................ A61F 9/00781 606/4 |
| 8,721,702 B2 | 5/2014 | Romoda et al. |
| 8,753,305 B2 | 6/2014 | Field et al. |
| 8,758,290 B2 | 6/2014 | Horvath et al. |
| 8,765,210 B2 | 7/2014 | Romoda et al. |
| 8,771,220 B2 | 7/2014 | Nissan et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,882,781 B2 | 11/2014 | Smedley et al. |
| 8,915,877 B2 | 12/2014 | Cunningham et al. |
| 8,932,247 B2 | 1/2015 | Stergiopulos |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Horvath et al. |
| 9,125,723 B2 | 9/2015 | Horvath et al. |
| 9,192,518 B2 | 11/2015 | Horvath et al. |
| 9,226,851 B2 | 1/2016 | Gunn |
| 9,271,869 B2 | 3/2016 | Horvath et al. |
| 9,283,115 B2 * | 3/2016 | Lind .................. A61F 9/00781 |
| 9,283,116 B2 | 3/2016 | Romoda et al. |
| 9,289,324 B2 * | 3/2016 | Johnson .............. A61F 9/00781 |
| 9,326,891 B2 | 5/2016 | Horvath et al. |
| 9,375,347 B2 | 6/2016 | Stergiopulos |
| 9,393,153 B2 | 7/2016 | Horvath et al. |
| 9,555,410 B2 | 1/2017 | Brammer et al. |
| 9,585,789 B2 | 3/2017 | Silvestrini et al. |
| 9,585,790 B2 | 3/2017 | Horvath et al. |
| 9,592,154 B2 | 3/2017 | Romoda et al. |
| 9,610,195 B2 | 4/2017 | Horvath |
| 9,636,254 B2 | 5/2017 | Yu et al. |
| 9,636,255 B2 | 5/2017 | Haffner et al. |
| 9,655,778 B2 | 5/2017 | Tyler |
| 9,655,779 B2 | 5/2017 | Bigler et al. |
| 9,693,900 B2 | 7/2017 | Gallardo Inzunza |
| 9,693,901 B2 | 7/2017 | Horvath et al. |
| 9,757,276 B2 | 9/2017 | Penhasi |
| 9,808,373 B2 | 11/2017 | Horvath et al. |
| 9,877,866 B2 | 1/2018 | Horvath et al. |
| 9,883,969 B2 | 2/2018 | Horvath et al. |
| 9,980,854 B2 | 5/2018 | Horvath et al. |
| 10,004,638 B2 | 6/2018 | Romoda et al. |
| 10,080,682 B2 | 9/2018 | Horvath et al. |
| 10,085,884 B2 | 10/2018 | Reitsamer et al. |
| 10,154,924 B2 | 12/2018 | Clauson et al. |
| 10,159,600 B2 | 12/2018 | Horvath et al. |
| 10,195,078 B2 | 2/2019 | Horvath et al. |
| 10,195,079 B2 | 2/2019 | Horvath et al. |
| 10,231,871 B2 | 3/2019 | Hill |
| 10,238,536 B2 | 3/2019 | Olson et al. |
| 10,285,853 B2 | 5/2019 | Man et al. |
| 10,307,293 B2 | 6/2019 | Horvath et al. |
| 10,314,743 B2 | 6/2019 | Romoda et al. |
| 10,322,267 B2 | 6/2019 | Hakim |
| 10,369,048 B2 | 8/2019 | Horvath et al. |
| 10,405,903 B1 | 9/2019 | Biesinger et al. |
| 10,335,030 B2 | 10/2019 | Alhourani |
| 10,342,703 B2 | 11/2019 | Siewert et al. |
| 10,463,537 B2 | 11/2019 | Horvath et al. |
| 10,470,927 B2 | 11/2019 | Horvath et al. |
| 10,363,168 B2 | 12/2019 | Schieber et al. |
| 10,492,948 B2 | 12/2019 | Baerveldt |
| 10,524,959 B2 | 1/2020 | Horvath |
| 10,524,958 B2 | 3/2020 | Camras et al. |
| 10,596,035 B2 | 4/2020 | Stergiopulos et al. |
| 10,758,412 B2 | 4/2020 | Velasquez |
| 10,716,663 B2 | 7/2020 | Salahieh et al. |
| 11,122,975 B2 | 1/2021 | Rodger et al. |
| 10,912,675 B2 | 2/2021 | Lubatschowski |
| 11,166,847 B2 | 2/2021 | Badawi et al. |
| 11,166,849 B2 | 2/2021 | Mixter et al. |
| 10,952,897 B1 | 3/2021 | Smith |
| 10,960,074 B2 | 3/2021 | Berdahl |
| 11,007,061 B2 | 5/2021 | Passman et al. |
| 11,039,954 B2 | 6/2021 | Cohen et al. |
| 11,058,581 B2 | 7/2021 | Mixter et al. |
| 11,065,154 B1 | 7/2021 | Sponsel et al. |
| 11,083,624 B2 | 8/2021 | Stein et al. |
| 11,166,848 B2 | 11/2021 | Mixter et al. |
| 11,291,585 B2 | 4/2022 | Schultz et al. |
| 11,517,477 B2 | 12/2022 | Lilly et al. |
| 11,529,258 B2 | 12/2022 | Chang et al. |
| 11,596,550 B2 | 3/2023 | Chang et al. |
| 11,737,920 B2 | 8/2023 | Chang et al. |
| 11,766,355 B2 | 9/2023 | Argento et al. |
| 11,865,283 B2 | 1/2024 | Schultz et al. |
| 12,220,350 B2 | 2/2025 | Mixter et al. |
| 12,226,343 B2 | 2/2025 | Mixter et al. |

(56) References Cited

U.S. PATENT DOCUMENTS

| | | |
|---|---|---|
| 2001/0011585 A1 | 8/2001 | Cassidy et al. |
| 2002/0177891 A1 | 11/2002 | Miles et al. |
| 2002/0193725 A1 | 12/2002 | Odrich |
| 2003/0079329 A1 | 5/2003 | Yaron et al. |
| 2003/0127090 A1 | 7/2003 | Gifford et al. |
| 2003/0163079 A1 | 8/2003 | Burnett |
| 2003/0183008 A1* | 10/2003 | Bang .............. B33Y 10/00 73/514.01 |
| 2004/0010219 A1 | 1/2004 | McCusker et al. |
| 2004/0162545 A1 | 8/2004 | Brown et al. |
| 2004/0190153 A1* | 9/2004 | Esch .............. A61F 2/1648 359/666 |
| 2004/0193095 A1 | 9/2004 | Shadduck |
| 2004/0254520 A1 | 12/2004 | Porteous et al. |
| 2005/0049578 A1 | 3/2005 | Tu et al. |
| 2005/0059956 A1 | 3/2005 | Varner et al. |
| 2005/0182350 A1 | 8/2005 | Nigam |
| 2005/0196424 A1 | 9/2005 | Chappa |
| 2006/0004317 A1 | 1/2006 | Mauge et al. |
| 2006/0069340 A1 | 3/2006 | Simon |
| 2006/0155300 A1* | 7/2006 | Stamper .............. A61F 9/00781 606/107 |
| 2006/0212113 A1 | 9/2006 | Shaolian et al. |
| 2006/0276739 A1 | 12/2006 | Brown |
| 2007/0010837 A1 | 1/2007 | Tanaka |
| 2007/0078371 A1 | 4/2007 | Brown et al. |
| 2007/0088432 A1 | 4/2007 | Solovay et al. |
| 2007/0265646 A1 | 11/2007 | McCoy et al. |
| 2007/0299487 A1 | 12/2007 | Shadduck |
| 2008/0077071 A1 | 3/2008 | Yaron et al. |
| 2008/0103440 A1 | 5/2008 | Ferren et al. |
| 2008/0119891 A1 | 5/2008 | Miles et al. |
| 2008/0125691 A1 | 5/2008 | Yaron et al. |
| 2008/0228127 A1 | 9/2008 | Burns et al. |
| 2008/0277332 A1 | 11/2008 | Liu |
| 2009/0012483 A1 | 1/2009 | Blott et al. |
| 2009/0036818 A1 | 2/2009 | Grahn et al. |
| 2009/0043321 A1 | 2/2009 | Conston et al. |
| 2009/0243956 A1 | 10/2009 | Keilman et al. |
| 2009/0259236 A2 | 10/2009 | Burnett et al. |
| 2009/0287136 A1 | 11/2009 | Castillejos |
| 2009/0314970 A1* | 12/2009 | McAvoy .............. F16K 99/0001 251/4 |
| 2009/0326432 A1 | 12/2009 | Schmidt et al. |
| 2009/0326517 A1 | 12/2009 | Bork et al. |
| 2010/0114006 A1 | 5/2010 | Baerveldt |
| 2010/0234791 A1 | 9/2010 | Lynch et al. |
| 2010/0241077 A1 | 9/2010 | Geipel et al. |
| 2010/0249691 A1 | 9/2010 | Van Der Mooren et al. |
| 2012/0035525 A1 | 2/2012 | Silvestrini |
| 2012/0065570 A1 | 3/2012 | Yeung et al. |
| 2012/0078220 A1 | 3/2012 | Fallin et al. |
| 2012/0089073 A1 | 4/2012 | Cunningham, Jr. |
| 2012/0232461 A1 | 9/2012 | Seaver et al. |
| 2013/0085440 A1* | 4/2013 | Bohm .............. A61F 9/00781 604/9 |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0236068 A1 | 8/2014 | Van Der Mooren et al. |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0257931 A1* | 9/2015 | Sanchez .............. A61F 9/00781 604/9 |
| 2015/0265469 A1 | 9/2015 | Olson et al. |
| 2015/0313603 A1 | 11/2015 | Bodewadt et al. |
| 2016/0058615 A1 | 3/2016 | Camras et al. |
| 2016/0067093 A1 | 3/2016 | Johnson et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0017279 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0028366 A1 | 2/2018 | Tout et al. |
| 2018/0092775 A1 | 4/2018 | de Juan, Jr. et al. |
| 2018/0147089 A1 | 5/2018 | Horvath et al. |
| 2018/0177633 A1 | 6/2018 | Haffner et al. |
| 2018/0206878 A1 | 7/2018 | Uspenski et al. |
| 2018/0250166 A1 | 9/2018 | Lubatschowski |
| 2018/0256320 A1 | 9/2018 | Millwee et al. |
| 2018/0333296 A1 | 11/2018 | Heitzmann et al. |
| 2019/0000673 A1 | 1/2019 | Field et al. |
| 2019/0021907 A1 | 1/2019 | Horvath et al. |
| 2019/0038462 A1 | 2/2019 | Vandiest |
| 2019/0038463 A1 | 2/2019 | Kasic |
| 2019/0046356 A1 | 2/2019 | Laroche |
| 2019/0060118 A1 | 2/2019 | Hill |
| 2019/0133826 A1 | 3/2019 | Horvath et al. |
| 2019/0121278 A1 | 4/2019 | Kawamura et al. |
| 2019/0142632 A1 | 5/2019 | Badawi et al. |
| 2019/0151079 A1 | 5/2019 | Zaldivar |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0254873 A1 | 8/2019 | Camras et al. |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0129332 A1 | 4/2020 | Van Der Mooren et al. |
| 2020/0170839 A1 | 6/2020 | Borrmann et al. |
| 2020/0179171 A1 | 6/2020 | Crimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0253725 A1 | 8/2020 | Hadba et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2020/0376239 A1 | 12/2020 | Heilman et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |

(56) References Cited

U.S. PATENT DOCUMENTS

| | | | |
|---|---|---|---|
| 2021/0069486 A1 | 3/2021 | Hakim | |
| 2021/0106462 A1 | 4/2021 | Sherwood et al. | |
| 2021/0128357 A1 | 5/2021 | de Juan, Jr. et al. | |
| 2021/0137736 A1 | 5/2021 | Cavuto et al. | |
| 2021/0137737 A1 | 5/2021 | Burns et al. | |
| 2021/0161713 A1 | 6/2021 | Bouremel et al. | |
| 2021/0196516 A1 | 7/2021 | Ianchulev | |
| 2021/0205132 A1 | 7/2021 | Horvath et al. | |
| 2021/0212858 A1 | 7/2021 | Tran et al. | |
| 2021/0251806 A1 | 8/2021 | Schultz et al. | |
| 2021/0282922 A1 | 9/2021 | Cohen-Tzemaeh et al. | |
| 2021/0298948 A1 | 9/2021 | Haffner et al. | |
| 2021/0315806 A1 | 10/2021 | Haffner | |
| 2021/0330499 A1 | 10/2021 | Wardle et al. | |
| 2022/0142818 A1 | 5/2022 | Chang et al. | |
| 2022/0160545 A1 | 5/2022 | Mixter et al. | |
| 2022/0160546 A1 | 5/2022 | Mixter et al. | |
| 2022/0168146 A1 | 6/2022 | Badawi et al. | |
| 2022/0202613 A1 | 6/2022 | Chang et al. | |
| 2022/0203078 A1 | 6/2022 | May | |
| 2022/0241565 A1 | 8/2022 | Nae et al. | |
| 2022/0265974 A1 | 8/2022 | Saul et al. | |
| 2022/0273491 A1 | 9/2022 | Brown | |
| 2022/0339035 A1 | 10/2022 | Lilly et al. | |
| 2022/0354695 A1 | 11/2022 | Badawi et al. | |
| 2022/0387216 A1 | 12/2022 | Schultz et al. | |
| 2022/0387217 A1 | 12/2022 | Argento et al. | |
| 2023/0086856 A1 | 3/2023 | Chang et al. | |
| 2023/0092196 A1 | 3/2023 | Argento et al. | |
| 2023/0201544 A1 | 6/2023 | Schultz et al. | |
| 2023/0233378 A1 | 7/2023 | Chang et al. | |
| 2023/0240891 A1 | 8/2023 | Lilly et al. | |
| 2023/0285192 A1 | 9/2023 | Chang et al. | |
| 2024/0139029 A1 | 5/2024 | Chang et al. | |
| 2024/0173169 A1 | 5/2024 | Schultz et al. | |
| 2024/0277522 A1 | 8/2024 | Schultz et al. | |
| 2024/0277523 A1 | 8/2024 | Schultz et al. | |
| 2024/0325697 A1 | 10/2024 | Schultz et al. | |
| 2024/0399122 A1 | 12/2024 | Bronez et al. | |
| 2025/0010044 A1 | 1/2025 | Schultz et al. | |

FOREIGN PATENT DOCUMENTS

| | | |
|---|---|---|
| AU | 2016201445 B2 | 3/2016 |
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3067172 | 12/2018 |
| CA | 3080713 | 5/2019 |
| CA | 3093160 | 9/2019 |
| CN | 101360523 A | 2/2009 |
| CN | 101965211 A | 2/2011 |
| CN | 103476371 | 12/2013 |
| CN | 104490515 | 4/2015 |
| CN | 106726124 | 5/2017 |
| CN | 108743016 A | 11/2018 |
| CN | 11405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1380317 | 1/2004 |
| EP | 1737531 A2 | 1/2007 |
| EP | 2552369 | 1/2017 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| GB | 2602434 | 9/2022 |
| HK | 1252748 | 5/2019 |
| HU | 043303 | 8/2019 |
| JP | 2001-523519 | 11/2001 |
| JP | 2013505065 | 2/2013 |
| JP | 5576427 B2 | 8/2014 |
| JP | 2017526504 | 9/2017 |
| JP | 2018-501010 | 1/2018 |
| JP | 2018519892 | 7/2018 |
| JP | 2018130580 | 8/2018 |
| JP | 2018529466 | 10/2018 |
| JP | 2019517366 | 6/2019 |
| JP | 201905934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO1992019294 | 11/1992 |
| WO | WO1996019249 | 6/1996 |
| WO | WO2004073564 | 9/2004 |
| WO | WO2004081613 | 9/2004 |
| WO | WO2007011302 A1 | 1/2007 |
| WO | WO2007087061 | 8/2007 |
| WO | WO2009111645 | 9/2009 |
| WO | WO2010111528 | 9/2010 |
| WO | WO2011034740 | 3/2011 |
| WO | WO2012040380 | 3/2012 |
| WO | WO2012113450 | 8/2012 |
| WO | WO2014130574 | 8/2014 |
| WO | WO2016/033270 | 3/2016 |
| WO | WO2016100500 | 6/2016 |
| WO | WO2016149425 | 9/2016 |
| WO | WO2016196841 A1 | 12/2016 |
| WO | WO2017058656 | 4/2017 |
| WO | WO2018229766 | 12/2018 |
| WO | WO2019018807 | 1/2019 |
| WO | WO2019094004 | 5/2019 |
| WO | WO2019094004 A1 | 5/2019 |
| WO | WO2019165053 | 8/2019 |
| WO | WO2019172940 | 9/2019 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020261184 | 12/2020 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |

(56) References Cited

FOREIGN PATENT DOCUMENTS

| | | |
|---|---|---|
| WO | WO2021188952 | 9/2021 |
| WO | WO2021204312 | 10/2021 |
| WO | WO2021212007 | 10/2021 |
| WO | WO2021230887 | 11/2021 |
| WO | WO2022159723 | 7/2022 |
| WO | WO2022175681 | 8/2022 |
| WO | WO2022220861 | 10/2022 |
| WO | WO2023004067 | 1/2023 |
| WO | WO2023278452 | 1/2023 |
| WO | WO2023009366 | 2/2023 |
| WO | WO2023063961 | 4/2023 |
| WO | WO2023064491 | 4/2023 |
| WO | WO2023091307 | 5/2023 |
| WO | WO2023107486 | 6/2023 |
| WO | WO2023215461 | 11/2023 |
| WO | WO2024026397 | 2/2024 |
| WO | WO2024030949 | 2/2024 |
| WO | WO2024097723 | 5/2024 |
| WO | WO2024097743 | 5/2024 |
| WO | WO2024220861 | 10/2024 |
| ZA | 201708295 | 5/2020 |

OTHER PUBLICATIONS

Extended European Search Report received for EP Application No. 20741616.5, Applicant: Shifamed Holdings, LLC, Date of Mailing: Oct. 5, 2022, 8 pages.
International Search Report and Written Opinion received for PCT Application No. PCT/US22/37747, filed on Jul. 20, 2022, Applicant: Shifamed Holdings, LLC, Date of Mailing: Dec. 6, 2022, 15 pages.
International Search Report and Written Opinion received for PCT Application No. PCT/US22/37917, filed on Jul. 21, 2022, Applicant: Shifamed Holdings, LLC, Date of Mailing: Dec. 15, 2022, 15 pages.
Keulegan et al. "Pressure Losses for Fluid Flow in Curved Pipes," Journal of Research of the National Bureau of Standards, vol. 18, Jan. 31, 1937 (Jan. 31, 1937), 26 pages.
Olsen et al. "Human sclera: thickness and surface area," American Journal of Ophthalmology, vol. 125, Issue. 2, https://pubmed.ncbi.nlm.nih.gov/9467451, Feb. 1, 1998 (Feb. 1, 1998), 1 page.
International Search Report and Written Opinion received for PCT Application No. PCT/US22/048863, filed on Nov. 3, 2022, Applicant: Shifamed Holdings, LLC, Date of Mailing: Feb. 16, 2023, 13 pages.
International Search Report and Written Opinion received for PCT Application No. PCT/US20/55144, filed on Oct. 9, 2020, Applicant: Shifamed Holdings, LLC, Date of Mailing: Feb. 1, 2021, 16 pages.
International Search Report and Written Opinion received for PCT Application No. PCT/US20/55141, filed on Oct. 9, 2020, Applicant: Shifamed Holdings, LLC, Date of Mailing: Jan. 29, 2021, 11 pages.
International Search Report and Written Opinion received for PCT Application No. PCT/US21/14774, filed on Jan. 22, 2021, Applicant: Shifamed Holdings, LLC, Date of Mailing: May 12, 2021, 10 pages.
International Search Report and Written Opinion received for PCT Application No. PCT/US21/17962, filed on Feb. 12, 2021, Applicant: Shifamed Holdings, LLC, Date of Mailing: Jun. 7, 2021, 12 pages.
International Search Report and Written Opinion received for PCT Application No. PCT/US21/23238, filed on Mar. 19, 2021, Applicant: Shifamed Holdings, LLC, Date of Mailing: Jul. 8, 2021, 10 pages.
International Search Report and Written Opinion received for PCT Application No. PCT/US21/18601, filed on Feb. 18, 2021, Applicant: Shifamed Holdings, LLC, Date of Mailing: Jul. 19, 2021, 12 pages.
International Search Report and Written Opinion received for PCT Application No. PCT/US21/27742, filed on Apr. 16, 2021, Applicant: Shifamed Holdings, LLC, Date of Mailing: Oct. 7, 2021, 13 pages.
International Search Report and Written Opinion received for PCT Application No. PCT/US18/43158, filed on Jul. 20, 2018, Applicant: Shifamed Holdings, LLC, Date of Mailing: Nov. 23, 2018, 12 pages.
International Search Report and Written Opinion received for PCT Application No. PCT/US20/41159, filed on Jul. 8, 2020, Applicant: Shifamed Holdings, LLC, Date of Mailing: Oct. 28, 2020, 13 pages.
International Search Report and Written Opinion received for PCT Application No. PCT/US20/41152, filed on Jul. 8, 2020, Applicant: Shifamed Holdings, LLC, Date of Mailing: Oct. 28, 2020, 13 pages.
International Search Report and Written Opinion received for PCT Application No. PCT/US20/14186, filed on Jan. 17, 2020, Applicant: Shifamed Holdings, LLC, Date of Mailing: Jun. 4, 2020, 13 pages.
International Search Report and Written Opinion received for PCT Application No. PCT/US21/49140, filed on Sep. 3, 2021, Applicant: Shifamed Holdings, LLC, Date of Mailing: Dec. 7, 2021, 22 pages.
International Search Report and Written Opinion received for PCT Application No. PCT/US21/55258, filed on Oct. 15, 2021, Applicant: Shifamed Holdings, LLC, Date of Mailing: Feb. 28, 2022, 18 pages.
International Search Report and Written Opinion received for PCT Application No. PCT/US22/13336, filed on Jan. 21, 2022, Applicant: Shifamed Holdings, LLC, Date of Mailing: Apr. 11, 2022, 9 pages.
International Search Report and Written Opinion received for PCT Application No. PCT/US22/52002, filed on Dec. 6, 2022, Applicant: Shifamed Holdings, LLC, Date of Mailing: Mar. 21, 2023, 11 pages.
International Search Report and Written Opinion received for PCT Application No. PCT/US22/46604, filed on Oct. 13, 2022, Applicant: Shifamed Holdings, LLC, Date of Mailing: Mar. 30, 2023, 11 pages.
International Search Report and Written Opinion received for PCT Application No. PCT/US23/80290, filed on Nov. 17, 2023, Applicant: Shifamed Holdings, LLC, Date of Mailing: May 15, 2024, 12 pages.
English translation of Japanese Office Action received for Application No. 2022-521301, Applicant: Shifamed Holdings, LLC, Date of Mailing: Jun. 3, 2024, 3 pages.
Extended European Search Report received for EP Application No. 23158246.1, Applicant: Shifamed Holdings, LLC, Date of Mailing: Aug. 7, 2023, 7 pages.
International Search Report and Written Opinion received for PCT Application No. PCT/US23/20973, filed on May 4, 2023, Applicant: Shifamed Holdings, LLC, Date of Mailing: Sep. 21, 2023, 15 pages.
Extended European Search Report received for EP Application No. 20874212.2, Applicant: Shifamed Holdings, LLC, Date of Mailing: Oct. 18, 2023, 8 pages.
Extended European Search Report received for EP Application No. 20875070.3, Applicant: Shifamed Holdings, LLC, Date of Mailing: Dec. 19, 2023, 7 pages.
International Search Report and Written Opinion received for PCT Application No. PCT/US23/71501, filed on Aug. 2, 2023, Applicant: Shifamed Holdings, LLC, Date of Mailing: Jan. 18, 2024, 20 pages.
Extended European Search Report received for EP Application No. 21744394.4, Applicant: Shifamed Holdings, LLC, Date of Mailing: Jan. 26, 2024, 7 pages.
Extended European Search Report received for EP Application No. 21787751.3; Applicant: Shifamed Holdings, LLC, Date of Mailing: Mar. 15, 2024, 8 pages.
International Search Report and Written Opinion received for PCT Application No. PCT/US23/71116, filed on Jul. 27, 2023, Applicant: Shifamed Holdings, LLC, Date of Mailing: Mar. 1, 2024, 12 pages.
Extended European Search Report received for EP Application No. 22743262.2; Applicant: Shifamed Holdings, LLC, Date of Mailing: Oct. 28, 2024, 8 pages.
Collins Dictionary, Textured definition and meaning, 2024, Collins Dictionary, https://www.collinsdictionary.com/dictionary/english/textured, Year: 2024, 1 page.

(56) References Cited

OTHER PUBLICATIONS

English translation of Chinese Office Action received for CN Application No. 201880060989.1; Applicant: Shifamed Holdings, LLC, Date of Mailing: Oct. 18, 2024, 9 pages.

English translation of Japanese Office Action received for Application No. 2022-521302; Applicant: Shifamed Holdings, LLC, Date of Mailing: Dec. 24, 2024, 7 pages.

Extended European Search Report received for EP Application No. 21937177.0, Applicant: Shifamed Holdings, LLC, Date of Mailing: Jan. 16, 2025, 6 pages.

\* cited by examiner

ADJUSTABLE FLOW GLAUCOMA SHUNTS AND METHODS FOR MAKING AND USING SAME

CROSS-REFERENCE TO RELATED APPLICATION(S)

This application is a 35 U.S.C. § 371 U.S. National Phase application of International Patent Application No. PCT/US2020/014186, filed Jan. 17, 2020, which claims the benefit of U.S. Patent Application No. 62/794,430, filed Jan. 18, 2019, and titled "ADJUSTABLE FLOW GLAUCOMA SHUNTS AND METHODS FOR MAKING AND USING SAME," the disclosures of which are incorporated herein by reference in their entireties.

TECHNICAL FIELD

The present technology relates to adjustable flow glaucoma shunts and methods for making and using such devices.

BACKGROUND

Glaucoma (e.g., ocular hypertension) is a disease associated with an increase in pressure within the eye resultant from an increase in production of aqueous humor (aqueous) within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the capillary bed in the sclera of the eye. Glaucoma typically results from a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

The present technology is directed to adjustable flow glaucoma shunts and methods for making and using such devices. In many of the embodiments disclosed herein, the adjustable flow glaucoma shunts comprise an adjustable fluid resistor ("resistor" within the context of this document refers to a fluid resistor), actuator, and/or actuation mechanism. Additionally, in certain embodiments, the shunts may also include an adjustable opening pressure control mechanism. These mechanisms can be selectively adjusted or modulated to increase or decrease the outflow resistance and/or opening pressure of the shunt in response to changes in any (or any combination of) intraocular pressure (IOP), aqueous production rate, native aqueous outflow resistance, and/or native aqueous outflow rate.

In one embodiment, for example, a variable flow shunt for treating glaucoma in a human patient comprises an elongated outflow tube having (a) a proximal inflow portion configured for placement within an anterior chamber in a region outside of an optical field of view of an eye of the patient, and (b) a distal outflow portion at a different location of the eye. The variable flow shunt further includes a flow control mechanism positioned along the outflow tube between the inflow portion and the outflow portion. The flow control mechanism comprises one or more control elements transformable between an open position that allows fluid to flow through the outflow tube and resistance positions that partially obstruct or attenuate fluid flow through the outflow tube. During operation, the control element(s) are movable between positions in response to non-invasive energy.

In another embodiment of the present technology, a shunt for treatment of glaucoma in a human patient comprises an elongated outflow drainage tube having a proximal inflow region and a distal outflow region. The shunt also includes an inflow control assembly at the proximal inflow region, and a transition region along the outflow tube between the inflow region and the outflow region. During operation, the transition region is transformable between a first shape and a second shape different than the first shape to inhibit or attenuate fluid flow through the outflow tube.

A method for treating glaucoma in a human patient in accordance with still another embodiment of the present technology can include positioning a variable flow shunt within an eye of the patient. The shunt comprises an elongated outflow drainage tube having a proximal inflow region at a first portion of the eye and a distal outflow region at a second, different portion of the eye. The method also includes transforming a flow control assembly carried by the elongated outflow drainage tube from a first configuration to second, different configuration to selectively control flow of aqueous through the variable flow shunt. Throughout the method, the flow control assembly may be actuated via non-invasive energy.

Specific details of various embodiments of the present technology are described below with reference to FIGS. 1A-6C. Although many of the embodiments are described below with respect to adjustable flow glaucoma shunts and associated methods, other embodiments are within the scope of the present technology. Additionally, other embodiments of the present technology can have different configurations, components, and/or procedures than those described herein. For instance, shunts configured in accordance with the present technology may include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Implantable Shunts for Glaucoma Treatment

Glaucoma is a degenerative ocular condition characterized by an increase in pressure within the eye resultant from an increase in production of aqueous humor (aqueous) within the eye and/or a decrease in the rate of outflow of aqueous from within the eye into the blood stream. The early stages of glaucoma are typically treated with drugs (e.g., eye drops). When drug treatments no longer suffice, however, surgical approaches may be used. Surgical or minimally invasive approaches primarily attempt to increase the outflow of aqueous from the anterior chamber to the blood stream either by the creation of alternative fluid paths or the augmentation of the natural paths for aqueous outflow.

Figures 1A, 1B:
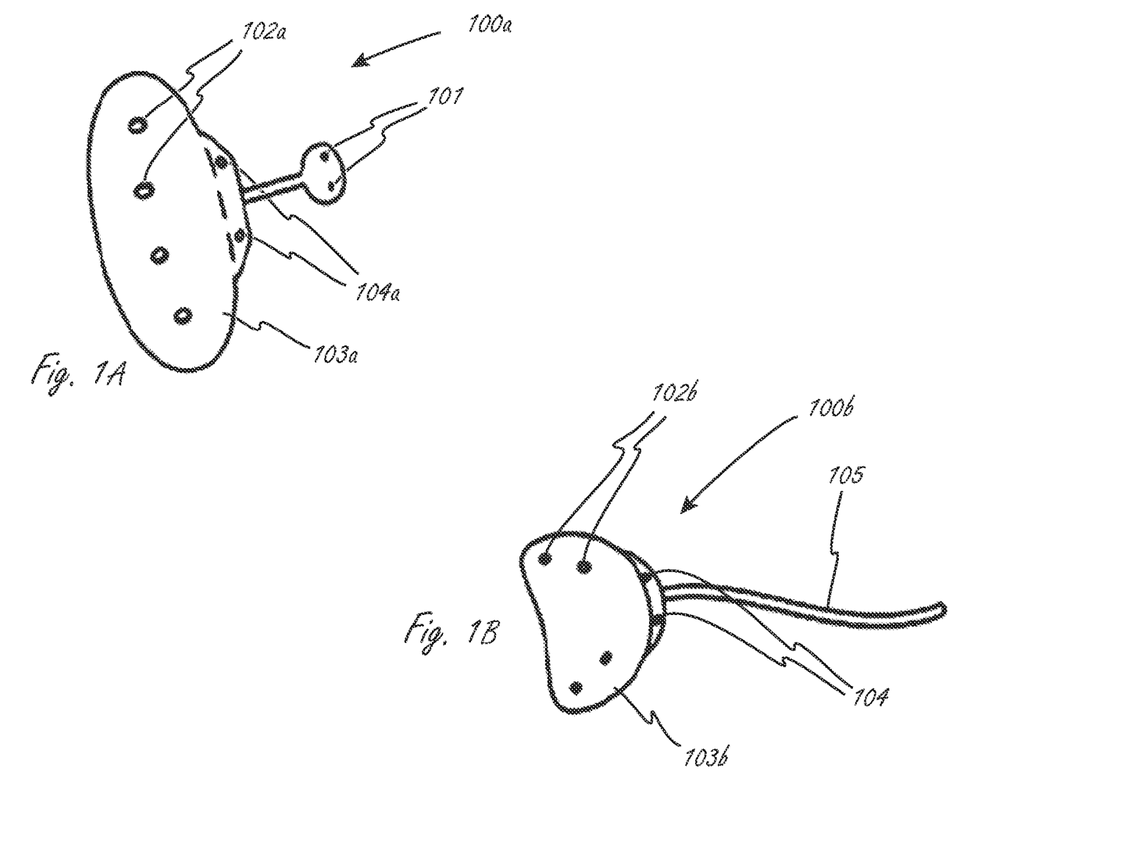
FIGS. 1A-1C illustrate glaucoma plate shunts configured to provide constant resistance to flow.
Figure 1C:
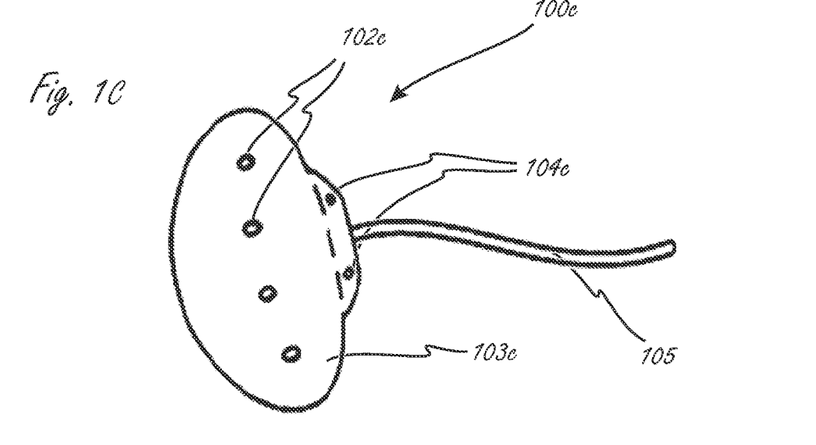

Devices used to lower outflow resistance are generally referred to as "glaucoma shunts" or "shunts." FIGS. 1A-1C, for example, illustrate several different traditional glaucoma plate shunts 100 (identified individually as 100a-c) configured to provide constant resistance to flow. The shunt 100a of FIG. 1A, for example, includes a plate 103a, a plurality of outflow ports 102a, one or more inflow ports 101, and tie-downs or engagement features 104a. The shunts 100b and 100c shown in FIGS. 1B and 1C, respectively, include several features similar to the features of shunt 100a. For example, these shunts 100b-c include plates 103b-c, outflow ports 102b-c, and tie-downs or engagement features 104b-c. The shunts 100b-c, however, include an inflow tube 105 instead of the inflow ports 101 of the shunt 100a.

Figure 2A:
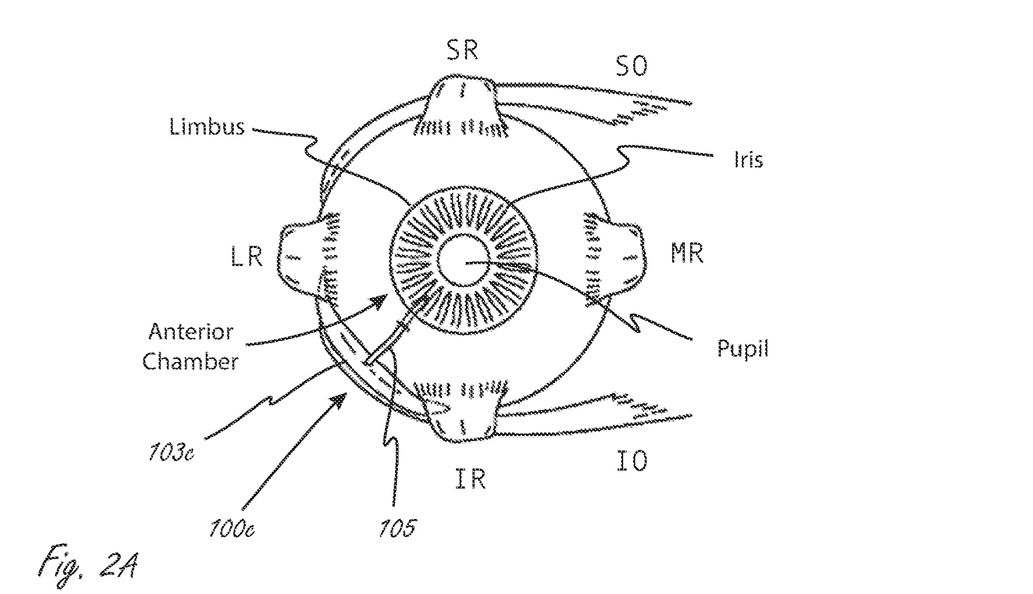
FIG. 2A is simplified front view of an eye E with an implanted shunt.
Figure 2B:
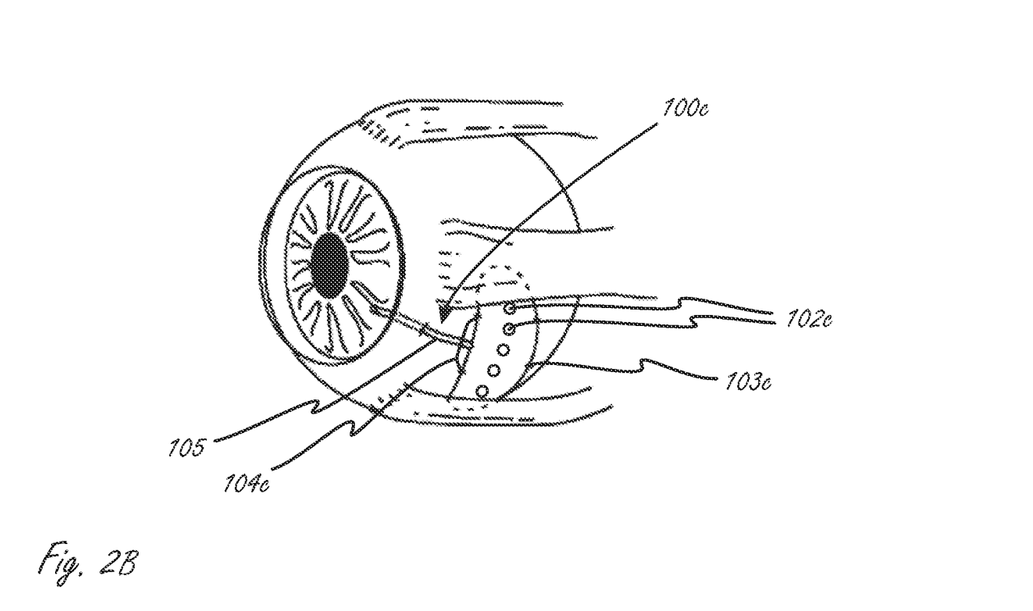
FIG. 2B is an isometric view of the eye capsule of FIG. 2A.

FIGS. 2A and 2B illustrate a human eye E and suitable location(s) in which shunts 100a-c may be implanted within the eye. More specifically, FIG. 2A is a simplified front view of the eye E, and FIG. 2B is an isometric view of the eye capsule of FIG. 2A. Referring first to FIG. 2A, the eye E includes a number of muscles to control its movement, including a superior rectus SR, inferior rectus IR, lateral rectus LR, medial rectus MR, superior oblique SO, and inferior oblique 10. The eye E also includes an iris, pupil, and limbus.

Referring to FIGS. 2A and 2B together, shunt 100c is positioned such that inflow tube 105 is positioned in an anterior chamber of the eye, and outflow ports 102c are positioned at a different location within the eye. Depending upon the design of the device, the outflow ports 102c may be place in a number of different suitable outflow locations (e.g., between the choroid and the sclera, between the conjunctiva and the sclera). For purposes of illustration, only shunt 100c is shown implanted in the eye E. It will be appreciated, however, that shunts 100a-b may be similarly implanted within the eye E.

Outflow resistance changes over time as the outflow location goes through its healing process after surgical implantation of the device. Because the outflow resistance changes over time, in many procedures the shunt (e.g., shunts 100a-c) is modified at implantation to temporarily increase its outflow resistance. After a period of time deemed sufficient to allow for healing of the tissues and stabilization of the outflow resistance, the modification to the shunt is reversed, thereby decreasing the outflow resistance. Such modifications can be invasive, time-consuming, and expensive for patients. If such a procedure is not followed, however, the likelihood of creating hypotony and its resultant problems is high. Accordingly, the present technology provides variable flow glaucoma shunts that enable a user to remotely actuate a flow control mechanism to selectively alter the flow of fluid through the shunt. The selectively adjustable shunts may be similar in certain aspects to those described in PCT Patent Publication No. 2019/018807, titled "ADJUSTABLE FLOW GLAUCOMA SHUNTS AND METHODS FOR MAKING AND USING SAME," the disclosure of which is incorporated by reference herein in its entirety.

Selected Embodiments of Variable Flow Glaucoma Shunts

Figure 3A:
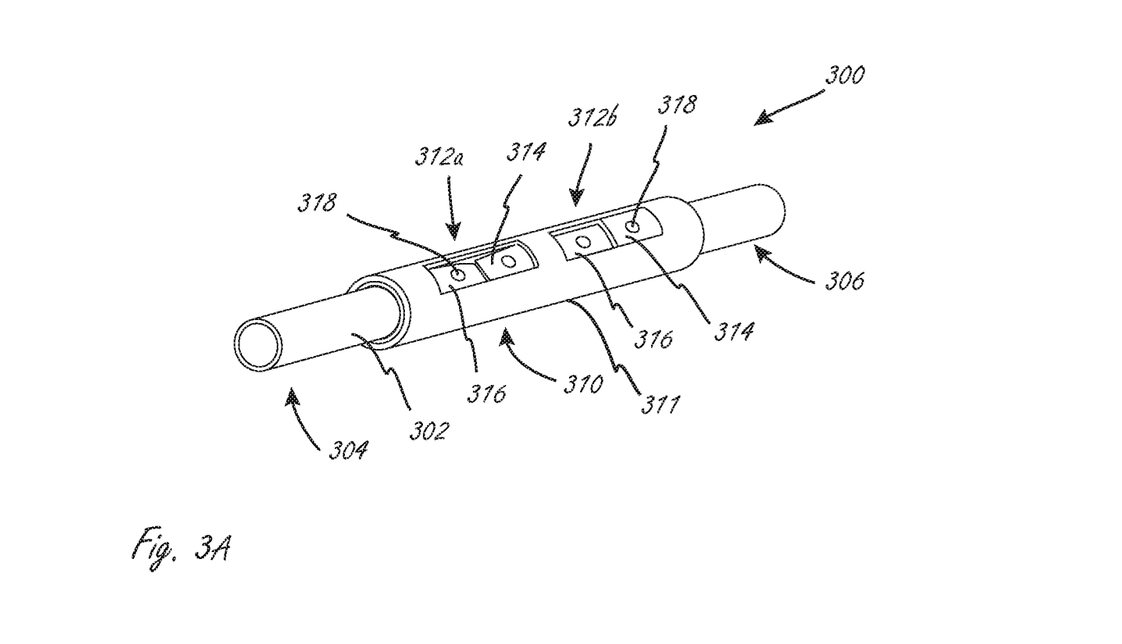
FIGS. 3A and 3B illustrate an adjustable flow glaucoma shunt configured in accordance with an embodiment of the present technology.

FIGS. 3A-6C illustrate a number of different embodiments for variable flow glaucoma shunt devices, along with particular components and features associated with such devices. FIG. 3A, for example, illustrates a variable flow glaucoma shunt 300 ("shunt 300") configured in accordance with an embodiment of the present technology. The shunt 300 includes an elongated drainage tube 302 (e.g., a fine bore length of thin walled tubing) having a proximal portion with an inflow portion 304 and a distal outflow portion 306 opposite the proximal portion. The inflow portion 304 of the shunt 300 is configured for placement within an anterior chamber in a region outside of the optical field of view of the eye, but within a region visible through the cornea. For purposes of illustration, the outflow portion 306 is shown relatively adjacent to the inflow portion 304. It will be appreciated, however, that the drainage tube 302 is sized and shaped to span a region between the anterior chamber and a desired outflow location within the eye of the patient (e.g., a bleb space).

The shunt 300 further includes a flow control mechanism 310 positioned along the drainage tube 302 and configured to act as a variable resistor during operation and selectively control flow of fluid through the drainage tube 302. In the illustrated embodiment, for example, the flow control mechanism 310 comprises a body portion 311 slidably positioned along the drainage tube 302. In other embodiments, however, the flow control mechanism 310 may be carried by or engaged with the drainage tube 302 in a different arrangement. The flow control mechanism 310 includes one or more control elements 312 (two are shown in the illustrated embodiment as a first control element 312a and a second control element 312b). The flow control elements 312a-b are configured to be selectively activated by non-invasive energy (e.g., a surgical laser, light, heat, etc.) and, upon activation, pivotably move into the flow path through the drainage tube 302 to inhibit/attenuate flow therethrough. In various embodiments, flow is modified in some manner (e.g., pressure and/or flow) between the activated and non-activated configurations. In various embodiments, activation inhibits and/or attenuates flow through the drainage tube. One will appreciate from the description herein that activation may refer to selecting or moving between one of a variety of positions or configurations of the flow control mechanism. Further, in various embodiments, in the non-activated configuration, the drainage tube 302 is fully open. In various embodiments, in the activated configuration, the drainage tube is fully closed, thus preventing/inhibiting fluid flow through the drainage tube 302.

Figure 3B:
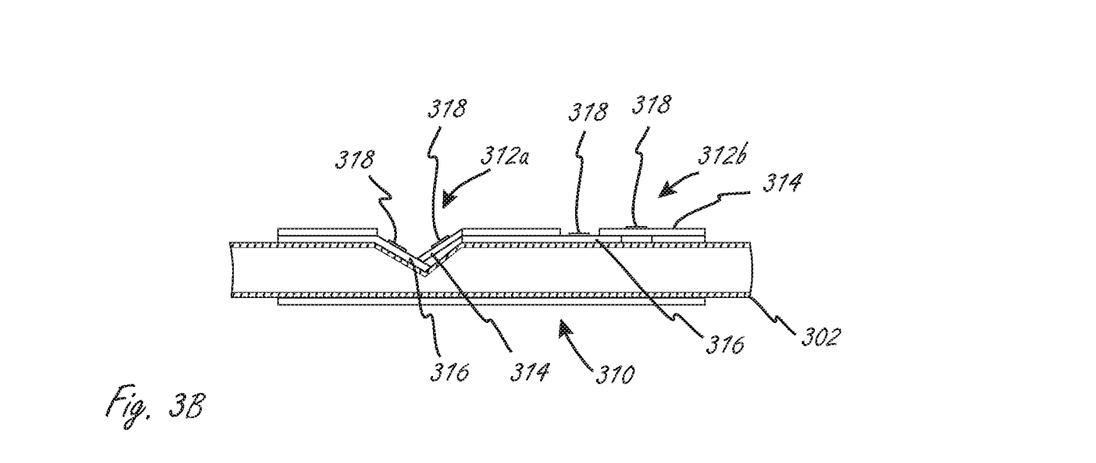

FIG. 3B, for example, is a partially schematic cross-sectional side view of the shunt 300 during operation. Referring to FIGS. 3A and 3B together, the first control element 312a includes a first finger 314 and a second finger 316. The first and second fingers 314 and 316 are pivotably movable relative to each other and the drainage tube 302 to transform the flow control mechanism 310 between an open configuration and a variety of different partially closed configurations (up to a fully closed configuration). In the illustrated embodiment, the first finger 314 is positioned to partially overlap the second finger 316. In other embodiments, however, the first and second fingers 314 and 316 may have a different arrangement relative to each other.

The first and second fingers 314 and 316 also each include target indicia or marker(s) 318 ("targets 318"). One or more individual targets 318 are included on each of the first and second fingers 314 and 316 and positioned as markers/targets for non-invasive energy used to selectively activate the flow control mechanism 310. The first and second fingers 314 and 316 are composed of a shape memory material (e.g., nitinol) and adapted to pivotably move when such non-invasive energy is applied. For example, applying heat to the first finger 314 (e.g., non-invasive energy applied to target(s) 318 on the first finger 314) can induce this feature to depress or move downward, thereby pushing the corresponding second finger 316 into the flow path (as best seen in FIG. 3B). Likewise, applying heat to the second finger 316 can induce this feature to lift/pivotably move upward, thereby pushing the corresponding first finger 314 upward and back toward an initial, non-obstructive position within the flow path. The first finger 314 and/or second finger 316 can be selectively activated via the non-invasive energy to provide precise control over the flow control element 312 and the resulting fluid flow via the drainage tube 302.

In the illustrated embodiment, the shunt 300 includes two flow control elements 312a and 312b positioned adjacent each other along the drainage tube 302. In other embodiments, however, the shunt 300 may include a different number of flow control elements 312 (e.g., a single flow control element 312 or greater than two flow control elements 312). Further, the individual flow control elements 312 may have a different arrangement relative to each other along the drainage tube 302.

Figure 4A:
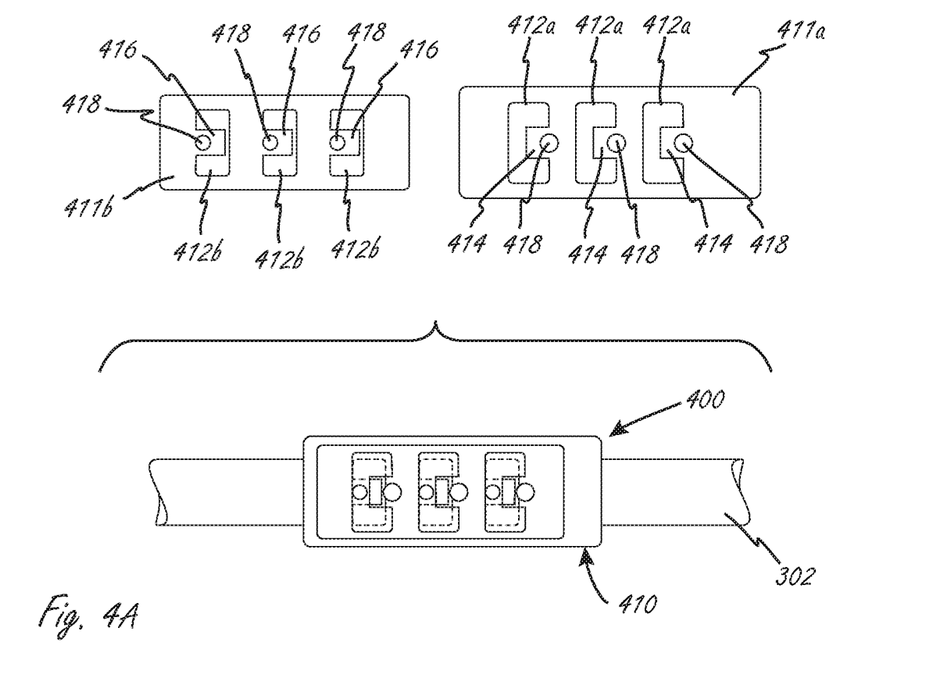
FIGS. 4A and 4B illustrate an adjustable flow glaucoma shunt configured in accordance with another embodiment of the present technology.
Figure 4B:
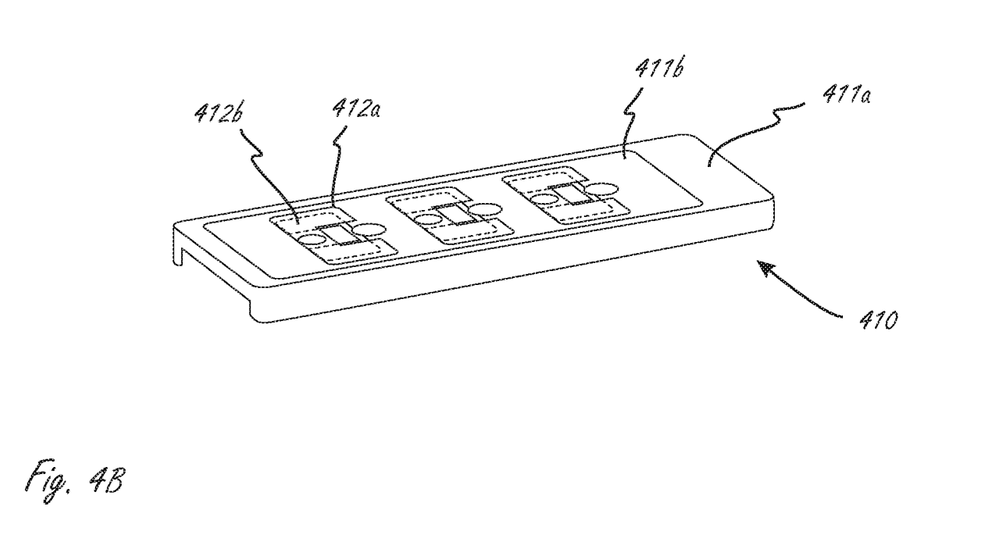

FIGS. 4A and 4B illustrate a shunt 400 configured in accordance with anther embodiment of the present technology. The shunt 400 includes a flow control mechanism 410 configured for use with the drainage tube 302 (or another suitable drainage tube), and configured to act as a variable resistor and selectively control flow of fluid through the tube. The shunt 400 includes several features similar to the features of the shunt 300 described above with reference to FIGS. 3A and 3B. For example, FIG. 4A is a partially exploded view of the shunt 400 showing individual components of the shunt 400, and FIG. 4B is an isometric view of the assembled flow control mechanism 410 before installation with the drainage tube 302. Referring to FIGS. 4A and 4B together, the shunt 400 includes a flow control mechanism 410 positioned along the drainage tube 302. Flow control mechanism 410 comprises a first plate 411a configured to be engaged with the drainage tube 302, and a second plate 411b configured to be operably coupled with or engaged with the first plate 411a. The flow control mechanism 410 further comprises a plurality of first flow control elements 412a carried by the first plate 411a, and a plurality of second flow control elements 412b carried by the second plate 411b. The first and second flow control elements 412a and 412b are positioned to be aligned when the first plate 411a and the second plate 411b are joined together and mated in a stacked configuration.

When engaged with the drainage tube 302, the flow control mechanism 410 is configured to function in a similar fashion to the flow control mechanism 310 described above with reference to FIGS. 3A and 3B. For example, the first flow control elements 412a each include a first finger 414 pivotably movable relative to the drainage tube 302 to transform the flow control mechanism 410 between an open configuration and a variety of different partially closed configurations (up to a fully closed configuration) in which the flow path through the drainage tube 302 is inhibited/attenuated (see, for example, the arrangement shown in FIG. 3B). The second flow control elements 412b each include a second finger 416 pivotably movable relative to the drainage tube 302 to engage the corresponding first fingers 414 and lift the first fingers 414 to transform the flow control mechanism 410 between the partially closed (or fully closed) configuration to a more open (or fully open) configuration. The first and second flow control elements 412a and 412b also each include target indicia or marker(s) 418. The targets 418 are positioned as markers/targets for non-invasive energy used to selectively activate the first and second flow control elements 412a and 412b during operation of the shunt 400.

In the illustrated embodiment, the flow control mechanism 410 of the shunt 400 includes three first flow control elements 412a and three second flow control elements 412b. In other embodiments, however, the shunt 400 may include a different number of flow control elements 412 and/or the individual flow control elements 412 may have a different arrangement relative to each other. In some embodiments, for example, the flow control elements 412 may be oriented in the opposite direction as that shown in FIGS. 4A and 4B.

Figure 5A:
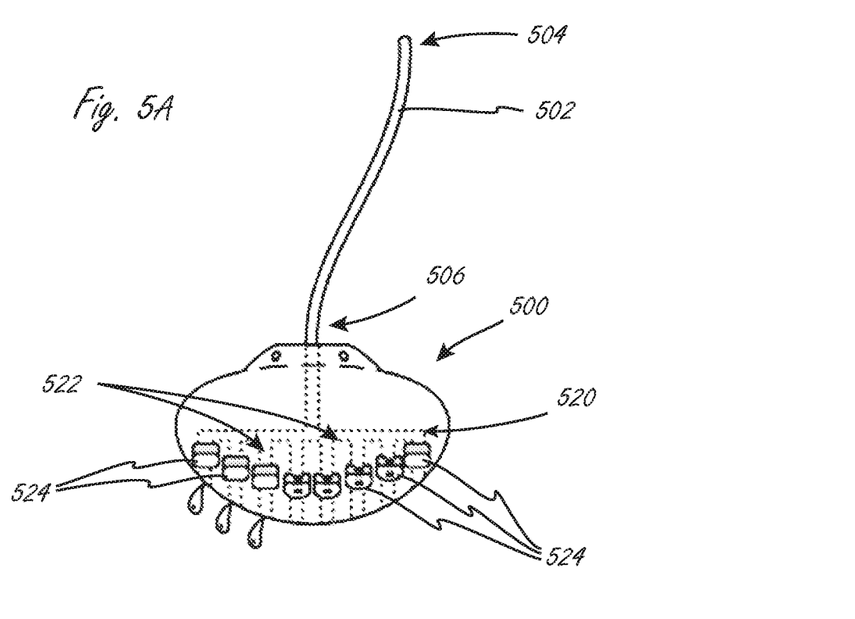
FIGS. 5A-5C illustrate a variable fluid resistor device configured in accordance with an embodiment of the present technology.
Figure 5B:
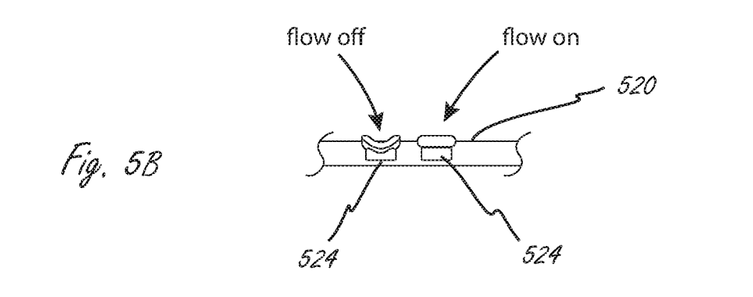

FIGS. 5A-5C illustrate a variable fluid resistor shunt 500 ("shunt 500") configured in accordance with an embodiment of the present technology. Referring to FIGS. 5A and 5B together, for example, drainage tube 502 comprises a first portion 504 and a second portion 506 opposite the first portion. A manifold 520 (e.g., a variable resistor assembly) is engaged with the drainage tube 502 and positioned at or adjacent with the second portion 506. The manifold 520 comprises multiple parallel lumens 522 arrayed across the width of the manifold 520 (FIG. 5A). For example, the manifold 520 can comprise two, three, four, five, six, or more lumens 522. When implanted in an eye, the manifold 520 can reside within a desired outflow location (e.g., a bleb space) or within a desired inflow location (e.g., an anterior chamber). Accordingly, the shunt 500 can be configured such that flow goes in either direction through the shunt 500.

Figure 5C:
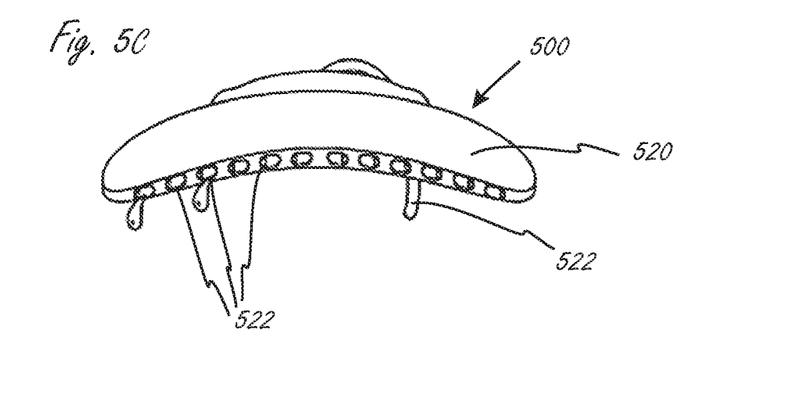

Each of the lumens 522 further comprises a flow control element 524. As best seen in FIG. 5B, individual flow control elements 524 are transformable between a first (e.g., open) position in which flow is not impeded and a second (e.g., closed) position in which flow through the corresponding lumen 522 is blocked or attenuated. The flow control elements 524 are all individually addressable (e.g., via non-invasive energy or other suitable mechanisms) such that flow through each of the lumens 522 can be selectively controlled. Referring to FIG. 5C, for example, flow through a majority of the lumens 522 has been attenuated or blocked via the corresponding flow control elements 524, but flow through the three lumens 522 on the leftmost portion of the manifold 520 remains open. It will be appreciated that selectively controlling flow via the manifold 520 allows for precise variable control of fluid outflow via the shunt 500. Further, in other embodiments, the manifold 520 of the shunt 500 may include a different number of lumens 522 and/or flow control elements 524, and the flow control elements 524 may have a different configuration.

In some embodiments, the lumens 522 may each have the same flow resistance. In embodiments in which the lumens 522 have the same flow resistance, opening additional lumens 522 is expected to result in a generally linear increase in the drainage rate, and blocking lumens 522 is expected to result in a generally linear decrease in the drainage rate. For example, moving from a single open lumen to two open lumens is expected to generally double the drainage rate, while moving from two open lumens to three open lumens is expected to generally increase the drainage rate by 50 percent.

In other embodiments, however, the lumens 522 may have different flow resistances. Flow resistance through the lumens 522, and thus drainage rates through the lumens 522, can be varied based on, for example, a length of the lumen and/or a diameter of the lumen. The length of the lumen is generally proportional to the flow resistance of the lumen, whereas the diameter of the lumen is generally inversely proportional to the flow resistance of the lumen. Accordingly, each individual lumen 522 may have a unique length, diameter, or length and diameter combination that gives it a certain flow resistance. Individual channels can then be selectively opened (or closed) to achieve a desired flow rate.

Figure 6A:
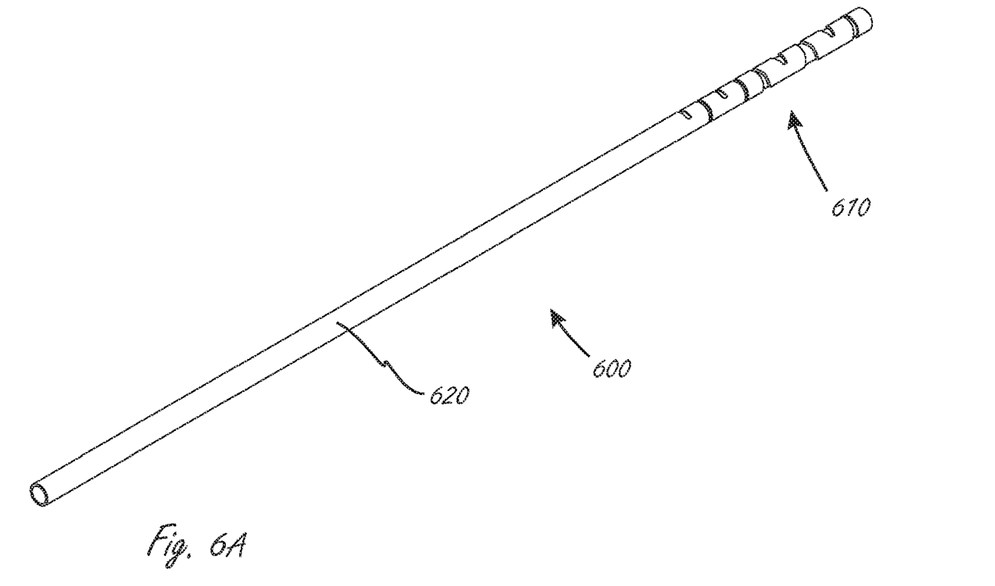
FIGS. 6A-6C illustrate an adjustable flow glaucoma shunt configured in accordance with still another embodiment of the present technology.
Figure 6B:
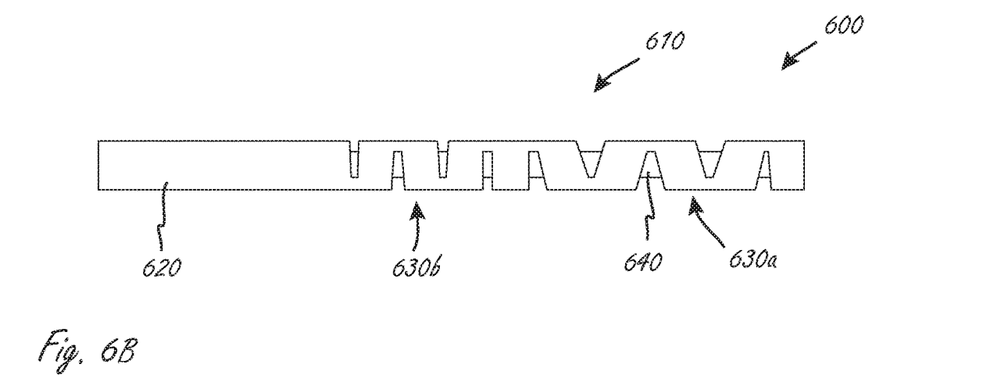
Figure 6C:
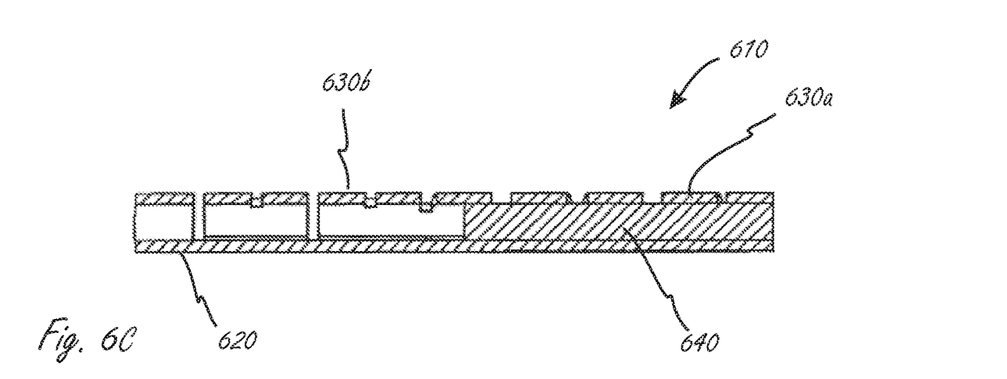

FIGS. 6A-6C illustrate an adjustable flow glaucoma shunt 600 ("shunt 600") configured in accordance with still another embodiment of the present technology. Referring first to FIG. 6A, for example, the shunt 600 includes an inflow control assembly 610 and an outflow drainage tube or outflow assembly 620. The inflow control assembly 610 is configured for placement within an anterior chamber in a region outside of the optical field of view of the eye, but within a region visible through the cornea. The outflow drainage tube 620 comprises tubing (e.g., a fine bore length of thin walled tubing) sized and shaped to span the region between the anterior chamber and a desired outflow location. As described in greater detail below, the inflow control assembly 610 comprises a control mechanism configured to act as a variable resistor during operation.

FIG. 6B is an enlarged view of the inflow control assembly 610 shown in operation. As best seen in FIG. 6B, the inflow control assembly 610 includes a first spring element 630a and a second spring element 630b arranged adjacent each other. In the illustrated embodiment, the first and second spring elements 630a and 630b are integrally formed from the same tube using a laser cutting process. In other embodiments, however, the first and second spring elements 630a and 630b may be separate, discrete components formed from different materials (e.g., nitinol, shape memory material, etc.). Further, it will be appreciated that the cut pattern, cut profile, and/or cut sizes within the tube may be optimized to increase/decrease flow through the spring elements 630a and 630b. The inflow control assembly 610 further includes a core element or plug feature 640 slidably received within an inner portion of the inflow control assembly 610 and selectively engaged with a selected spring element 630a or 630b.

As best seen in FIGS. 6B and 6C, in operation, the first and second spring elements 630a and 630b are configured to be selectively activated by non-invasive energy and, upon activation, expand to allow flow through the corresponding spring body (i.e., the helical cuts in the tube), as well as compress the opposing spring element. The core element 640 extends approximately the length of one of the spring elements (the first spring element 630a in the illustrated arrangement) and can be positioned such that when the first spring element 630a opens, there is little or no flow path therethrough. During further operation of the shunt 600, the compressed second spring element 630b can be targeted with non-invasive energy (e.g., laser energy), which causes the second spring element 630b to expand/actuate, while causing the first spring element 630a to compress, thereby oscillating the shunt 600 and selectively controlling the flow therethrough.

In further embodiments, the inflow control assembly 610 of the shunt 600 may include one or more additional spring elements 630 positioned to be actuated to selectively control fluid flow. Further, in some embodiments the shunt 600 can include a thermal isolation element positioned between the individual springs to help further ensure that only one spring actuates at a time after delivery of non-invasive energy. The thermal isolation element(s) are an optional feature that may not be included in some embodiments.

In many of the embodiments described herein, the actuators or fluid resistors are configured to introduce features that selectively impede or attenuate fluid flow through the drainage tube during operation. In this way, the actuators/fluid resistors can incrementally or continuously change the flow resistance through the drainage tube to selectively regulate pressure/flow. The actuators and fluid resistors configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the drainage tube.

The disclosed actuators and fluid resistors can all be operated using non-invasive energy. This feature allows such devices to be implanted in the patient and then modified/adjusted over time without further invasive surgeries or procedures for the patient. Further, because the devices disclosed herein may be actuated via non-invasive energy, such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

Examples

Several aspects of the present technology are set forth in the following examples.

1. A variable flow shunt for treatment of glaucoma in a human patient, the variable flow shunt comprising:
   an elongated outflow tube having (a) a proximal inflow portion configured for placement within an anterior chamber in a region outside of an optical field of view of an eye of the patient, and (b) a distal outflow portion at a different location of the eye; and
   a flow control mechanism positioned along the outflow tube between the inflow portion and the outflow portion, wherein the flow control mechanism comprises one or more control elements transformable between an open position that allows fluid to flow through the outflow tube and at least one resistance position that reduces fluid flow through the outflow tube,
   wherein during operation, the one or more control elements are movable between the open position and the at least one resistance position in response to non-invasive energy.

2. The variable flow shunt of example 1 wherein the one or more control elements are transformable between a first resistance position that provides a first level of reduction of fluid flow, and a second resistance position that provides a second level of reduction of fluid flow greater than the first level of reduction.

3. The variable flow shunt of example 1 wherein the one or more control elements are transformable between a first resistance position that provides a first level of flow reduction and a plurality of second resistance positions that provide increasing levels of flow reduction.

4. The variable flow shunt of example 1 or example 2 wherein the one or more control elements are configured to partially obstruct fluid flow through the outflow tube in the at least one resistance position by changing a diameter and/or a cross-sectional shape of a flow path through the outflow tube.

5. The variable flow shunt of any one of examples 1–4 wherein the one or more control elements are movable between the open position and the at least one resistance position in response to laser energy.

6. The variable flow shunt of any one of examples 1-5 wherein the one or more control elements are configured to hold the open position or the at least one resistance position without power.

7. The variable flow shunt of example 1 wherein at least one control element comprises:
 a first finger pivotably movable between a first, open position in which the first finger is out of a flow path through the outflow tube and one or more second resistance positions in which the first finger impedes fluid flow along the flow path; and
 a second finger engaged with the first finger and configured to pivotably move the first finger from the one or more one or more second resistance positions toward the first open position,
 wherein the first and second fingers are pivotably movable in response to the non-invasive energy.

8. A shunt for treatment of glaucoma in a human patient, the shunt comprising:
 an elongated outflow drainage tube having a proximal inflow region and a distal outflow region;
 an inflow control assembly at the proximal inflow region; and
 a transition region along the outflow tube between the inflow region and the outflow region, wherein, during operation, the transition region is transformable between a first shape and a second shape different than the first shape to inhibit and/or attenuate fluid flow through the outflow tube.

9. The shunt of example 8 wherein the transition region is configured to transform between the first shape and the second shape upon application of non-invasive energy to one or more selected areas of the transition region.

10. The shunt of example 9 wherein the non-invasive energy is laser energy.

11. A method for treating glaucoma in a human patient, the method comprising:
 positioning a variable flow shunt within an eye of the patient, wherein the shunt comprises an elongated outflow drainage tube having a proximal inflow region at a first portion of the eye and a distal outflow region at a second, different portion of the eye; and
 transforming a flow control assembly carried by the elongated outflow drainage tube from a first configuration to a second, different configuration to selectively control flow of aqueous through the variable flow shunt,
 wherein the flow control assembly is actuated via non-invasive energy.

12. The method of example 11 wherein transforming the flow control assembly carried by the elongated outflow drainage tube comprises actuating the flow control assembly, via the non-invasive energy, to pivotably move a control element of the control assembly into a flow path of the drainage tube such that flow along the flow path is attenuated.

13. The method of example 12, further comprising actuating the flow control assembly, via the non-invasive energy, to pivotably move the control element out of the flow path of the drainage tube such that flow along the flow path is returned to a non-attenuated state.

14. An adjustable flow shunt for treating glaucoma in a human patient, the shunt comprising:
 an elongated outflow drainage tube having a proximal inflow region and a distal outflow region; and
 an inflow control assembly at the proximal inflow region, wherein the inflow control assembly comprises—
  a first spring element;
  a second spring element positioned adjacent to the first element; and
  a core element sized and shaped to be slidably received within one of the first or second spring elements,
 wherein the first spring element is configured to be selectively activated by non-invasive energy and, upon activation, expand such that (a) the second spring element positioned adjacent the first spring element is compressed, and (b) the expansion selectively allows fluid flow through the expanded first spring element.

15. The adjustable flow shunt of example 14 wherein the inflow control assembly is configured for placement within an anterior chamber in a region outside of the optical field of view of the eye.

16. The adjustable flow shunt of example 14 or example 15 wherein the spring element is configured to be activated via laser energy.

17. The adjustable flow shunt of any one of examples 14-16 wherein the spring element is composed of a shape memory material.

18. The adjustable flow shunt of any one of examples 14-16 wherein the spring element is composed of nitinol.

19. A variable fluid resistor shunt for treatment of glaucoma, the variable fluid resistor shunt comprising:
 an elongated drainage tube having a first portion configured to be in fluid communication with a fluid chamber in an eye of a human patient and a second portion opposite the first portion;
 a variable resistor assembly configured to selectively control flow of fluid through the drainage tube, wherein the variable resistor assembly comprises—
  a base portion;
  multiple fluid lumens arranged in an array across the base portion in fluid communication with the drainage tube; and
  a plurality of flow control elements, wherein each fluid lumen includes a flow control element positioned to selectively control fluid flow along the corresponding fluid lumen;
 wherein, during operation, the individual flow control elements are configured to be selectively targeted and actuated via non-invasive energy to change each flow control element between a first open position in which fluid can flow through the corresponding fluid lumen and a second at least partially closed position in which fluid flow through the corresponding fluid lumen is reduced.

20. The variable fluid resistor shunt of example 19 wherein at least two of the multiple fluid lumens have a different flow resistance when the corresponding flow control element is in the first open position.

21. The variable fluid resistor shunt of example 19 or example 20 wherein the multiple fluid lumens include a first lumen and a second lumen, and wherein the first lumen has a first diameter and the second lumen has a second diameter greater than the first diameter.

22. The variable fluid resistor shunt of any of examples 19-21 wherein the multiple fluid lumens include a first lumen and a second lumen, and wherein the first lumen has a first length and the second lumen has a second length greater than the first length.

23. The variable fluid resistor shunt of example 19 wherein each of the multiple fluid lumens have the same flow resistance when the corresponding flow control element is in the first open position.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the variable flow shunts described herein may be combined with any of the features of the other variable flow shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with variable flow shunts have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A variable flow shunt for treatment of glaucoma in a human patient, the variable flow shunt comprising:
    an elongated outflow tube having (a) a proximal inflow portion configured for placement within an anterior chamber in a region outside of an optical field of view of an eye of the patient, and (b) a distal outflow portion at a different location of the eye; and
    a flow control mechanism positioned along the outflow tube between the inflow portion and the outflow portion, wherein the flow control mechanism comprises two actuation elements in contact with and partially overlapping each other, wherein the two actuation elements are selectively actuatable to pivotably move the flow control mechanism between an open position that allows fluid to flow through the outflow tube and at least one resistance position that reduces fluid flow through the outflow tube, and wherein the actuation elements include—
        a first actuation element selectively actuatable to move the flow control mechanism from the open position to the at least one resistance position, and
        a second actuation element selectively actuatable to move the flow control mechanism from the resistance position back toward the open position, and
    wherein, during operation, the flow control mechanism is pivotably movable between the open position and the at least one resistance position in response to non-invasive laser energy.

2. The variable flow shunt of claim 1 wherein the flow control mechanism is pivotably movable between a first resistance position that provides a first level of reduction of fluid flow, and a second resistance position that provides a second level of reduction of fluid flow greater than the first level of reduction.

3. The variable flow shunt of claim 1 wherein the flow control mechanism is pivotably movable between a first resistance position that provides a first level of flow reduction and a plurality of second resistance positions that provide increasing levels of flow reduction.

4. The variable flow shunt of claim 1 wherein the flow control mechanism is configured to partially obstruct fluid flow through the outflow tube in the at least one resistance position by changing a cross-sectional shape of a flow path through the outflow tube.

5. The variable flow shunt of claim 1 wherein the actuation elements are configured to hold the flow control mechanism in the open position or the at least one resistance position without power.

6. The variable flow shunt of claim 1 wherein:
    the first actuation element comprises a first finger pivotably movable between a first, open position in which the first finger is out of a flow path through the outflow tube and one or more second resistance positions in which the first finger impedes fluid flow along the flow path; and
    the second actuation element comprises a second finger c, wherein the second finger is engaged with the first finger and configured to pivotably move the first finger from the one or more one or more second resistance positions toward the first open position,
    wherein the first and second fingers are pivotably movable in response to the non-invasive laser energy.

7. A shunt for treatment of glaucoma in a human patient, the shunt comprising:
    an elongated outflow drainage tube having an inflow region and an outflow region; and
    a transition region along the outflow tube between the inflow region and the outflow region, wherein the transition region comprises a first actuation element and a second actuation element in contact with and partially overlapping the first actuation element, and
    wherein, during operation—
        the first actuation element of the transition region is actuatable to change the transition region from a first cross-sectional shape to a second cross-sectional shape different than the first cross-sectional shape to inhibit and/or attenuate fluid flow through the outflow tube, and the second actuation element of the transition region is actuatable to change the transition region from the second cross-sectional shape back toward the first cross-sectional shape to increase fluid flow through the outflow tube, and wherein the transition region is configured to transform between the first cross-sectional shape and the second cross-sectional shape upon application of non-invasive laser energy to one or more selected areas of the transition region.

8. A method for treating glaucoma in a human patient, the method comprising:

positioning a variable flow shunt within an eye of the patient, wherein the shunt comprises— an elongated outflow drainage tube having a proximal inflow region at a first portion of the eye and a distal outflow region at a second, different portion of the eye; and a flow control assembly carried by the elongated outflow drainage tube, wherein the flow control assembly includes a first actuation element and a second actuation element in contact with and partially overlapping each other, wherein the first actuation element is selectively actuatable to move the flow control assembly from a first configuration in which flow of aqueous along a flow path of the drainage tube is not impeded to a second, different configuration in which the flow of aqueous is attenuated, and wherein the second actuation element is selectively actuatable to move the flow control mechanism from the second configuration back toward the first configuration; and transforming the flow control assembly carried by the elongated outflow drainage tube, via laser energy from an energy source external to the patient, to pivotably move the first actuation element of the flow control assembly from the first configuration to the second configuration to selectively reduce the flow of aqueous along the flow path.

9. The method of claim 8, further comprising transforming the flow control assembly, via the laser energy, to pivotably move the second actuation element of the flow control assembly from the second configuration back toward the first configuration such that the first and second actuation elements are moved out of the flow path of the drainage tube and flow along the flow path is returned to a non-attenuated state.

10. The variable flow shunt of claim 1 wherein the actuation elements are composed of a shape memory material.

11. The shunt of claim 7 wherein the transition region is composed, at least in part, of a shape memory material.

12. The method of claim 8, further comprising pivotably moving the first actuation element, via the laser energy, to a plurality of additional second configurations that provide increasing levels of flow attenuation along the flow path through the drainage tube.

13. The method of claim 8 wherein transforming the flow control assembly from the first configuration to the second configuration comprises changing a cross-sectional shape of the flow path through the drainage tube.

14. The method of claim 8 wherein the first and second actuation elements are composed, at least in part, of a shape memory material.

15. The variable flow shunt of claim 1 wherein the two actuation elements are positioned to move together during operation.

* * * * *